United States Patent [19]

Michel et al.

[11] Patent Number: 4,826,847
[45] Date of Patent: May 2, 1989

[54] BETA-BLOCKING OXINDOLE DERIVATIVES

[75] Inventors: Helmut Michel, Mannheim; Wolfgang Kampe, Heddesheim; Klaus Strein, Hemsbach; Wolfgang Bartsch, Viernheim, all of Fed. Rep. of Germany

[73] Assignee: Boehringer Mannheim GmbH, Mannheim, Fed. Rep. of Germany

[21] Appl. No.: 948,422

[22] Filed: Dec. 30, 1986

Related U.S. Application Data

[63] Continuation of Ser. No. 755,497, Jul. 16, 1985, abandoned.

[30] Foreign Application Priority Data

Jul. 18, 1984 [DE] Fed. Rep. of Germany ....... 3426419

[51] Int. Cl.$^4$ ................. A61K 31/505; C07D 401/06; C07D 403/06
[52] U.S. Cl. .................................. 514/256; 514/274; 514/323; 514/339; 514/359; 514/381; 514/383; 514/386; 514/392; 514/397; 514/403; 514/406; 514/409; 514/414; 514/418; 544/310; 544/333; 546/201; 546/273; 548/253; 548/255; 548/262; 548/269; 548/301; 548/318; 548/336; 548/371; 548/372; 548/374; 548/411; 548/455; 548/467; 548/486
[58] Field of Search ................. 544/310, 333; 546/201, 546/273; 548/253, 255, 267, 269, 301, 318, 336, 371, 372, 374, 411, 454, 467, 486, 455; 514/256, 274, 323, 339, 381, 359, 383, 386, 392, 397, 403, 406, 409, 414, 415, 418

[56] References Cited

U.S. PATENT DOCUMENTS

| 3,825,558 | 7/1974 | Seemann | 548/486 |
| 3,882,143 | 5/1975 | Seemann | 548/486 |
| 4,115,409 | 9/1978 | Large et al. | 548/486 |
| 4,161,530 | 7/1979 | Koella | 514/418 |
| 4,256,890 | 3/1981 | Nakagawa et al. | 546/158 |
| 4,287,194 | 9/1981 | Kosa et al. | 514/418 |
| 4,288,452 | 9/1981 | Sombroek et al. | 514/651 |
| 4,317,832 | 3/1982 | Klingler et al. | 514/418 |
| 4,642,309 | 2/1987 | Michel et al. | 548/467 |

FOREIGN PATENT DOCUMENTS 3310891 9/1984 Fed. Rep. of Germany ...... 548/486

OTHER PUBLICATIONS

*Burger's Medicinal Chemistry*, 4th Edit., Part III, 1981, pp. 310–316.

Primary Examiner—Richard A. Schwartz
Attorney, Agent, or Firm—Felfe & Lynch

[57] ABSTRACT

The present invention provides oxindole derivatives of the formula:

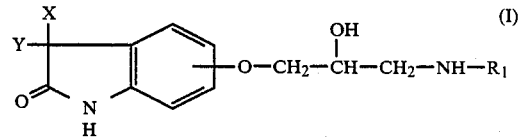

wherein the various substituents are defined hereinbelow.

The above compounds display nitrate-like as well as β-blocking actions.

13 Claims, No Drawings

BETA-BLOCKING OXINDOLE DERIVATIVES

This is a continuation of application Ser. No. 755,497, filed July 16, 1985, now abandoned.

The present invention is concerned with new oxindole derivatives, processes for the preparation thereof and pharmaceutical compositions containing them, as well as intermediates for the preparation thereof.

The new oxindole derivatives according to the present invention are compounds of the general formula:

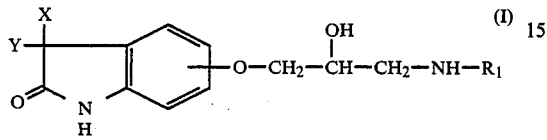

wherein $R_1$ is a $C_2$–$C_{10}$ nitratoalkyl radical, X is a hydrogen atom or a $C_1$–$C_6$-alkyl radical and Y is a hydrogen atom, a $C_1$–$C_6$-alkyl radical or, together with X and the carbon atom to which they are attached, forms a $C_3$–$C_7$-cycloalkyl ring, or is a radical of the general formula:

wherein $R_2$ is a hydrogen atom or, together with X, represents a valency bond, $R_3$ is a hydrogen atom or a straight-chained or branched $C_1$–$C_6$-alkyl radical and $R_4$ is a straight-chained or branched $C_1$–$C_6$-alkyl radical, a cycloalkyl radical or an optionally substituted aryl or a mono- or bicyclic-hetero radical as defined below or $R_3$ and $R_4$ together with the C-atom represent a $C_3$–$C_7$-cycloalkylene radical optionally interrupted by the group

in which $R_5$ is a hydrogen atom or a $C_1$–$C_6$-alkyl radical: and the pharmacologically acceptable salts thereof.

The aryl and hetaryl radicals can optionally be substituted one or more times by halogen, $C_1$–$C_6$-alkyl, hydroxyalkyl, hydroxyl, $C_1$–$C_6$-alkoxy, $C_2$–$C_4$-alkenyl, $C_2$–$C_4$-alkenyloxy, $C_2$–$C_4$-alkynyl, amino, $C_1$–$C_4$-alkylamino, $C_2$–$C_8$-dialkylamino, aminocarbonyl, $C_1$–$C_4$-alkylaminocarbonyl, $C_2$–$C_8$-dialkylaminocarbonyl, cyano, $C_2$–$C_4$-alkanoyl, aminosulphonyl, $C_1$–$C_4$-alkylaminosulphonyl, $C_2$–$C_8$-dialkylaminosulphonyl, carboxyl, $C_1$–$C_6$-alkoxycarbonyl, $C_1$–$C_6$-alkylthio, $C_1$–$C_6$-alkylsulphinyl, $C_1$–$C_6$-alkylsulphonyl, $C_2$–$C_4$-alkanoylamido, $C_1$–$C_4$-alkylsulphonylamido or nitro groups or by a $C_1$–$C_2$-alkylenedioxy radical. However, as mentioned above, $R_3$ and $R_4$ can together with the C-atom also represent a $C_3$–$C_7$-cyclo-alkylene radical optionally interrupted by the group

wherein $R_5$ is a hydrogen atom or a $C_1$–$C_6$-alkyl radical.

Since the compounds of general formula (I) possess either one asymmetric carbon atom or, when Y is a radical of the general formula

and X and $R_2$ each represent hydrogen atoms, possess two asymmetric carbon atoms, the present invention also provides the optically-active forms and racemic mixtures of these compounds.

When X and $R_2$ together represent a valency bond in compounds of general formula (I), the E- and Z-isomers are also provided by the present invention.

The compounds according to the present invention, as well as their pharmacologically acceptable salts, display, in the same dosage range, nitrate-like as well as β-blocking actions and can, therefore, be used for the treatment and prophylaxis of circulatory and heart diseases, for example high blood pressure and angina pectoris.

The $C_2$–$C_{10}$-nitratoalkyl radicals of the substituents $R_1$ are straight-chained or branched radicals, for example nitratoethyl, nitratopropyl, nitratobutyl, nitratopentyl, nitratohexyl, 1-methyl-2-nitratoethyl, 1-methyl-3-nitratopropyl, 1,1-dimethyl-3-nitratopropyl, 1,3-dimethyl-3-nitratopropyl or 2,2-dimethyl-3-nitratopropyl radicals. However, the 1-methyl-3-nitratopropyl, 1,1-dimethyl-3-nitratopropyl and 1,3-dimethylnitratopropyl radicals are especially preferred.

By $C_1$–$C_6$-alkyl radicals in the substituents $R_3$, $R_4$, $R_5$, X and Y are to be understood straight-chained and branched radicals, for example methyl, ethyl, n-propyl, isopropyl, n-butyl, isobutyl, tert.-butyl and n-hexyl radicals. However, methyl, ethyl, isopropyl and tert.-butyl radicals are preferred.

By $C_3$–$C_7$-cycloalkyl rings which are formed by X and Y and the carbon atom to which they are attached, there are preferably to be understood cyclopropyl, cyclopentyl, cyclohexyl and cycloheptyl radicals.

Cycloalkyl radicals in the case of substituent $R_4$ are especially the cyclopentyl and cyclohexyl radicals.

Aryl radicals in the case of the substituents $R_4$ are preferably phenyl radicals.

The alkyl, alkoxy, alkylthio, alkylsulphinyl, alkylsulphonyl, alkoxycarbonyl, alkylaminocarbonyl, dialkylaminocarbonyl, alkylaminosulphonyl, dialkylaminosulphonyl, alkanoyl, alkylsulphonylamido, dialkylamino and alkanoylamido radicals which can be substituents of the aryl and hetaryl radicals contain 1–8 and preferably 1–6 carbon atoms. The methyl and ethyl radicals, as well as the various isomeric propyl, butyl and pentyl radicals, are especially preferred.

In the case of the alkenyl and alkynyl radicals, the allyl and propargyl radicals are especially preferred.

By halogen, within the meaning of the present invention, there are to be understood fluorine, chlorine, bromine and iodine, fluorine, chlorine and bromine being preferred.

By mono- or bicyclic-hetero radicals $R_4$, according to the present invention, there are to be understood mono- and bicyclic radicals with one or more heteratoms. Preferred radicals include the furan, thiophene, pyrrole, pyrazole, imidazole, triazole, tetrazole, imidazolinone, pyridine, pyrimidine, uracil, indole, indazole and dihydropyran radicals.

Preferred cycloalkyl rings, which can be formed together with the C-atom, are cyclopropyl, cyclopentyl and cyclohexyl. Preferred rings interrupted by the group

are pyrrolidine and piperidine. Methyl and Ethyl are preferred $R_5$ substituents.

The preparation of the compounds of general formula (I) can be carried out in known manner by (a) reacting a compound of the general formula:

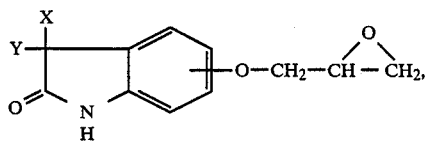

wherein X and Y have the same meanings as above, with a compound of the general formula:

$$H_2-N-R_1 \quad (III),$$

in which $R_1$ has the same meaning as above; or (b) condensing a compound of general formula (II), in which X and Y are hydrogen atoms, with a compound of the general formula:

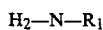

in which $R_3$ and $R_4$ have the same meanings as above, and subsequently reacting with a compound of general formula (III); or (c) reducing a compound of the general formula:

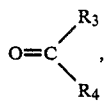

in which $R_6$ is a group which can be split off, and reacting with a compound of general formula (III); and cyclising the compound thereby obtained of the general formula:

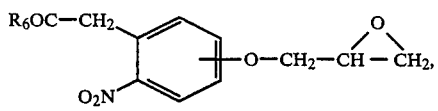

in which $R_1$ and $R_6$ have the same meanings as above; or (d) reacting a compound of the general formula:

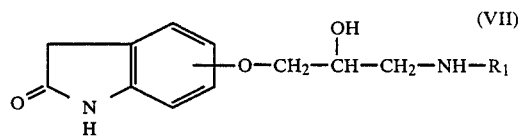

in which $R_1$ has the same meaning as above, with a compound of general formula (IV); or (e) reacting a compound of the general formula:

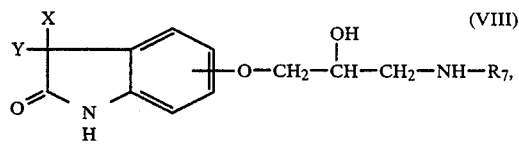

in which X and Y have the same meanings as above and $R_7$ is a $C_2$—$C_{10}$-hydroxyalkyl radical, with nitric acid or a reactive derivative thereof;

whereafter, if desired, the compound obtained is converted into a compatible salt.

The preparation of compounds of general formula (II), as well as of some representatives thereof, especially those which are 4-substituted, is described in Federal Republic of Germany Patent Specification No. P 33 10 891.1. New compounds can be prepared in an analogous manner.

Compounds of general formulae (III) and (IV) can be prepared by processes known from the literature or are commonly available.

Some of the compounds of general formula (V) are described in European Patent Specification No. 00 149 28 and new compounds can be prepared analogously.

The compounds of general formula (VI) are new. Thus, the present invention also provides the new intermediates of general formula (VI) for the preparation of compounds of general formula (I).

Groups in compounds of general formulae (V) and (VI) which can be split off include amino, imidazolyl, hydroxyl and $C_1$-$C_6$-alkoxy radicals, hydroxyl, methoxy, ethoxy and propoxy radicals being preferred.

The reaction of compounds of general formula (VII) with compounds of general formula (IV) can be carried out without the use of a solvent or in an inert solvent, for example methanol, ethanol n-butanol, diethyl ether, methylene chloride, toluene, ethyl acetate, tetrahydrofuran, dioxan, dimethylformamide or dimethyl sulphoxide, with the addition of an appropriate catalyst, for example, ammonia, triethylamine, N-ethyldiisopropylamine, tributylamine, piperidine, morpholine, 1-methylpiperidine, 4-methylmorpholine or sodium methylate. However, especially preferred are methanol, ethanol and dimethyl sulphoxide, as well as triethylamine, piperidine and 1-methylpiperidine.

Compounds of general formula (VII) are themselves pharmacologically effective but can also be used as intermediates for the preparation of other active compounds of general formula (I).

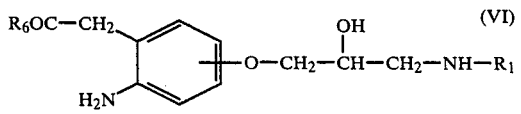

The compounds of general formula (I) according to the present invention can be obtained in the form of racemic mixtures. The separation of the racemate into the optically-active forms take place by known methods via the diastereomeric salts of optically-active acids, for example tartaric acid, malic acid or camphorsulphonic acid.

Compounds of general formula (VIII) are also new and form part of the subject matter of the present invention. The preparation of these compounds is preferably carried out by reacting epoxides of general formula (II) or (V) with a compound of the general formula:

$$H_2N-R_7 \qquad (IX),$$

in which $R_7$ has the same meaning as above.

The reaction with nitric acid or with a reactive derivative thereof, for example nitronium tetrafluoroborate, is preferably carried out with acetonitrile.

For converting the compounds of general formula (I) into their pharmacologically acceptable salts, these are reacted, preferably in an organic solvent, with the equivalent amount of an inorganic or organic acid, for example hydrochloric acid, hydrobromic acid, phosphoric acid, sulphuric acid, acetic acid, citric acid, tartaric acid, maleic acid, fumaric acid, benzoic acid or cyclohexylsulphamic acid.

For the preparation of pharmaceuticals, the compounds of general formula (I) are mixed in known manner with appropriate pharmaceutical carrier substances, aroma, flavouring and colouring materials and formed, for example, into tablets or dragees or, with the addition of appropriate adjuvants, suspended or dissolved in water or in an oil, for example olive oil.

The new compounds of general formula (I) according to the present invention and the salts thereof can be administered enterally or parenterally in liquid or solid form. As injection medium, it is preferred to use water which contains the additives usual in the case of injection solutions, such as stabilising agents, solubilising agent or buffers.

Such additives include, for example, tartrate and citrate buffers, ethanol, complex forming agents (such as ethylenediamine-tetraacetic acid and the nontoxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening materials.

The compounds are administered in amounts of 20–500 mg per day, based on 75 kg body weight. It is preferable to administer this dosage gradually, either by administering 1–2 tablets with an active substance content of 10–200 mg, 2 or 3 times a day, or to use slow release formulations so that only once a day 1–2 tablets with 20–500 mg active substance can be administered. The active substance can also be administered by injection 1–8 times per day or by continuous infusion, amounts of 5–200 mg/day normally sufficing in that case.

TEST PROTOCOL

The compounds claimed have beta-blocking as well as nitrate-like properties and can therefore be used as antianginal therapy (heart disorder characterized by attacks of pain where there is an insufficiency of oxygen).

At present pharmaceuticals are available either for their nitrate-like properties, e.g. nitroglycerin, isosorbide dinitrate, isosorbide-5-mononitrate, or for their beta-blocker properties, e.g. propanolol, pindolol. Combinations of these drugs are also used, but so far no compound is available which by its working principle incorporates both qualities. The invention provides compounds which, surprisingly, have nitrate-like as well as beta-blocking qualities in overlapping dosage ranges. Thus, a single compound can be used to treat two separate (but usually related in occurrence) ailments.

Since such substances have so far not been developed specifically, a method for screening the nitrate-like action is not known. It is for this reason that the following method was developed:

(a) to show denitration properties (which constitutes the working principle of all nitrates; see U. Abshagen in Handbook of Experimental Pharmacology, Vol. 76, 1985, Chapter 10.) the denitration rate was evaluated in relation to that of the known isosorbide dinitrate metabolite isosorbide-5-mononitrate ($V_{rel}$). To that end, rats were killed under narcosis and their livers re-perfused 4 min with a corresponding concentrated equimolar ($5 \times 10^{-5}$M/l) solution of isosorbide-5-mononitrate and the substances to be tested respectively (a blood sediment solution was pumped through the liver vessels) and the freed amount in $NO_2$ determined in the perfusate (outflowing fluid). To have comparable conditions, the perfusion with isosorbide-5-mononitrate (standard substance) was administered as control at the second time as if it were an unknown substance (in this way a liver performance change under the test conditions can be recognized and accordingly allowed for).

High $V_{rel}$-values show a fast denitration, low values a slow denitration.

(b) The β-blocking effectiveness was shown by administering rabbits isoprenaline in an amount of 1 mcg/kg i.v. and determining the dose, which causes an inhibition of 50% of the increase of the frequency through isoprenaline (ID $50_{fcor}$=inhibition dose 50%).

TABLE

| Example | ID 50 fcor mcg/kg i.v. | Vrel | Example | ID 50 fcor mcg/kg i.v. | Vrel |
|---|---|---|---|---|---|
| Isosorbide-5-mononitrate | — | 0.86 | 1 (c) | 5083 | 1.77 |
| Isosorbide-dinitrate | — | 17.5 | 2 (c) | 1968 | 0.59 |
| Propranolol | 331 | — | 4 (a) | 9.6 | 0.65 |
| Pindolol | 104 | — | 1 (f) | — | 3.01 |
| 2 | 11 | 1.12 | 1 (i) | 3358 | 0.81 |
| 1 | 6.6 | 1.60 | BV 40 | 690 | 3.51 |
| 1 (b) | 3.8 | 2.02 | 4 (b) | 27.6 | 0.54 |
| 4 (h) | 39 | 1.39 | 1 (g) | 5308 | 0.70 |
| 1 (a) | 15 | 1.23 | 4 (j) | — | 0.49 |
| 1 (e) | — | 1.79 | BV 43 | 9.6 | 0.83 |
| 2 (a) | — | 2.40 | BV 2 | — | 2.99 |
| 4 (d) | 9.6 | 1.00 | 4 (k) | — | 1.88 |
| 1 (d) | — | 1.81 | BV 4 | 1095 | 1.22 |
| 4 (g) | 13 | 1.59 | BV 6 | >4000 | 0.74 |
| 2 (b) | 172 | 0.86 | BV 9 | 765 | 0.60 |
| 4 (f) | — | 1.80 | BV 20 | 113 | 0.71 |

EXAMPLES

Apart from the compounds described in the Examples, preferred compounds according to the present invention include the following:

1. 4-[2-hydroxy-3-(1-methyl-3-nitratopropylamino)-propoxy]-3-methylindolinone 2. 4-[2-hydroxy-3-(1-methyl-3-nitratopropylamino)-propoxy]-3,3-dimethylindolinone fumarate (m.p. 140°–142° C., recrystallised from ethanol; yield 40% of theory)
3. 4-[2-hydroxy-3-(1-methyl-3-nitratopropylamino)-propoxy]-3-spiro-tetramethyleneindolinone
4. 4-[2-hydroxy-3-(1-methyl-3-nitratopropylamino)-propoxy]-3-(3-chlorobenzylidene)-indolinone fumarate (m.p. 97°–100° C. recrystallised from propan-2-ol; yield 30% of theory)
5. 4-[2-hydroxy-3-(1-methyl-3-nitratopropylamino)-propoxy]-3-(2-fluorobenzylidene)-indolinone
6. 4-[2-hydroxy-3-(1-methyl-3-nitratopropylamino)-propoxy]-3-(2-methylbenzylidene)-indolinon fumarate (m.p. 80°–85° C. recrystallised from propan-2-ol, yield 20% of theory)
7. 4-[2-hydroxy-3-(1-methyl-3-nitratopropylamino)-propoxy]-3-(2-hydroxymethylbenzylidene)-indolinone
8. 4-[2-hydroxy-3-(1-methyl-3-nitratopropylamino)-propoxy]-3-(4-hydroxybenzylidene)-indolinone
9. 4-[2-hydroxy-3-(1-methyl-3-nitratopropylamino)-propoxy]-3-(3-methoxybenzylidene)-indolinone acetate (m.p. 80°–83° C. recrystallised from ethyl acetate, yield 25% of theory)
10. 4-[2-hydroxy-3-(1-methyl-3-nitratopropylamino)-propoxy]-3-(2-allyloxybenzylidene)-indolinone
11. 4-[2-hydroxy-3-(1-methyl-3-nitratopropylamino)-propoxy]-3-(4-aminobenzylidene)-indolinone
12. 4-[2-hydroxy-3-(1-methyl-3-nitratopropylamino)-propoxy]-3-(4-dimethylaminobenzylidene)-indolinone
13. 4-[2-hydroxy-3-(1-methyl-3-nitratopropylamino)-propoxy]-3-(2-acetamidobenzylidene)-indolinone
14. 4-[2-hydroxy-3-(1-methyl-3-nitratopropylamino)-propoxy]-3-(2-methanesulphonylamidobenzylidene)-indolinone
15. 4-[2-hydroxy-3-(1-methyl-3-nitratopropylamino)-propoxy]-3-(4-acetylbenzylidene)-indolinone
16. 4-[2-hydroxy-3-(1-methyl-3-nitratopropylamino)-propoxy]-3-(4-aminocarbonylbenzylidene)-indolinone
17. 4-[2-hydroxy-3-(1-methyl-3-nitratopropylamino)-propoxy]-3-(4-dimethylaminocarbonylbenzylidene)-indolinone
18. 4-[2-hydroxy-3-(1-methyl-3-nitratopropylamino)-propoxy]-3-(2-carboxybenzylidene)-indolinone
19. 4-[2-hydroxy-3-(1-methyl-3-nitratopropylamino)-propoxy]-3-(4-methoxycarbonylbenzylidene)-indolinone
20. 4-[2-hydroxy-3-(1-methyl-3-nitratopropylamino)-propoxy]-3-(4-nitrobenzylidene)-indolinone (m.p. 135°–137+ C. recrystallised from methanol, yield 30% of theory)
21. 4-[2-hydroxy-3-(1-methyl-3-nitratopropylamino)-propoxy]-3-(2-dimethylaminosulphonylbenzylidene)-indolinone
22. 4-[2-hydroxy-3-(1-methyl-3-nitratopropylamino)-propoxy]-3-(3-methoxy-4-hydroxybenzylidene)-indolinone
23. 4-[2-hydroxy-3-(1-methyl-3-nitratopropylamino)-propoxy]-3-(2-hydroxy-4-methylthiobenzylidene)-indolinone
24. 4-[2-hydroxy-3-(1-methyl-3-nitratopropylamino)-propoxy]-3-(3,4-methylenedioxybenzylidene)-indolinone
25. 4-[2-hydroxy-3-(1-methyl-3-nitratopropylamino)-propoxy]-3-(2-methylaminosulphonylfuran-5-yl)-methyleneindolinone
26. 4-[2-hydroxy-3-(1-methyl-3-nitratopropylamino)-propoxy]-3-(4-methylimidazolin-2-on-5-yl)-methyleneindolinone
27. 4-[2-hydroxy-3-(1-methyl-3-nitratopropylamino)-propoxy]-3-(pyridin-4-yl)-methyleneindolinone
28. 4-[2-hydroxy-3-(1-methyl-3-nitratopropylamino)-propoxy]-3-(5,6-dihydro-2H-pyran-3-yl)-methyleneindolinone
29. 4-[2-hydroxy-3-(1-methyl-3-nitropropylamino)-propoxy]-3-(indol-3-yl)-methyleneindolinone
30. 5-[2-hydroxy-3-(1-methyl-3-nitratopropylamino)-propoxy]-3-ethylideneindolinone
31. 5-[2-hydroxy-3-(1-methyl-3-nitratopropylamino)-propoxy]-3-ethylindolinone
32. 5-[2-hydroxy-3-(1-methyl-3-nitratopropylamino)-propoxy]-3-(2-methylpropylidene)-indolinone
33. 5-[2-hydroxy-3-(1-methyl-3-nitratopropylamino)-propoxy]-3-(2-methylpropyl)-indolinone
34. 5-[2-hydroxy-3-(1-methyl-3-nitratopropylamino)-propoxy]-3-cyclohexylmethyleneindolinone
35. 5-[2-hydroxy-3-(1-methyl-3-nitratopropylamino)-propoxy]-3-cyclohexylmethylindolinone
36. 5-[2-hydroxy-3-(1-methyl-3-nitratopropylamino)-propoxy]-3-cyclohexylideneindolinone
37. 5-[2-hydroxy-3-(1-methyl-3-nitratopropylamino)-propoxy]-3-cyclohexylindolinone
38. 5-[2-hydroxy-3-(1-methyl-3-nitratopropylamino)-propoxy]-3-(1-methylpiperidin-4-ylidene)-indolinone
39. 5-[2-hydroxy-3-(1-methyl-3-nitratopropylamino)-propoxy]-3-(1-methylpiperidyl-4)-indolinone
40. 4-[2-hydroxy-3-(2,2-dimethyl-3-nitratopropylamino)-propoxy]-indolinone hemifumarate (m.p. 154°–158° C., recrystallised from methanol; yield 35% of theory)
41. 4-[2-hydroxy-3-(1-methyl-3-nitratopropylamino)-propoxy]-3-benzylindolinone
42. 4-[2-hydroxy-3-(1-methyl-3-nitratopropylamino)-propoxy]-3-(pyrazol-5-yl)-methylindolinone (m.p. 127°–129° C., recrystallised from ethyl acetate; yield 25% of theory)
43. 4-[2-hydroxy-3-(1-methyl-3-nitratopropylamino)-propoxy]-3-(3-methylpyrazol-5-yl)-methyleneindolinone.

Preferred intermediates of general formula (VI) include the following:
2-[2-hydroxy-3-(1-methyl-3-nitratopropylamino)-propoxy]-6-aminophenyl acetic acid
2-[2-hydroxy-3-(1,1-dimethyl-3-nitratopropylamino)-propoxy]-6-aminophenyl acetic acid
2-[2-hydroxy-3-(1,3-dimethyl-3-nitratopropylamino)-propoxy]-6-aminophenyl acetic acid
2-[2-hydroxy-3-(2,2-dimethyl-3-nitratopropylamino)-propoxy]-6-aminophenyl acetic acid as well as the imidazolides, methyl and ethyl esters and other reactive derivatives thereof.

Apart from the compounds mentioned in the Examples, preferred intermediates of general formula (VIII) include the following:
5-[2-hydroxy-3-(1-methyl-3-hydroxypropylamino)-propoxy]-indolinone
4-[2-hydroxy-3-(1,1-dimethyl-3-hydroxypropylamino)-propoxy]-indolinone
4-[2-hydroxy-3-(1,3-dimethyl-3-hydroxypropylamino)-propoxy]-indolinone 4-[2-hydroxy-3-(2,2-dimethyl-3-hydroxypropylamino)-propoxy]-indolinone 4-[2-hydroxy-3-(1-methyl-3-hydroxypropylamino)-propoxy]-3-methylindolinone 4-[2-hydroxy-3-(1,1-dimethyl-3-hydroxypropylamino)-propoxy]-3-methylindolinone 5-[2-hydroxy-3-(1,1-dimethyl-3-hydroxypropylamino)-propoxy]-3-methylindolinone 4-[2-hydroxy-3-(1,3-dimethyl-3-hydroxypropylamino)-propoxy]-3-methylindolinone 4-[2-hydroxy-3-(2,2-dimethyl-3-hydroxypropylamino)-propoxy]-3-methylindolinone 4-[2-hydroxy-3-(1-methyl-3-hydroxypropylamino)-propoxy]-3,3-dimethylindolinone 4-[2-hydroxy-3-(1,1-dimethyl-3-hydroxypropylamino)-propoxy]-3,3-dimethylindolinone 4-[2-hydroxy-3-(1,3-dimethyl-3-hydroxypropylamino)-propoxy]-3,3-dimethylindolinone 5-[2-hydroxy-3-(1,3-dimethyl-3-hydroxypropylamino)-propoxy]-3,3-dimethylindolinone 4-[2-hydroxy-3-(2,2-dimethyl-3-hydroxypropylamino)-propoxy]-3,3-dimethylindolinone 4-[2-hydroxy-3-(1-methyl-3-hydroxypropylamino)-propoxy]-3-(pyrazol-5-yl)-methyleneindolinone 4-[2-hydroxy-3-(1,1-dimethyl-3-hydroxypropylamino)-propoxy]-3-(pyrazol-5-yl)-methyleneindolinone 4-[2-hydroxy-3-(1,3-dimethyl-3-hydroxypropylamino)-propoxy]-3-(pyrazol-5-yl)-methyleneindolinone 4-[2-hydroxy-3-(2,2-dimethyl-3-hydroxypropylamino)-propoxy]-3-(pyrazol-5-yl)-methyleneindolinone 5-[2-hydroxy-3-(2,2-dimethyl-3-hydroxypropylamino)-propoxy]-3-(pyrazol-5-yl)-methyleneindolinone.

The following Examples are given for the purpose of illustrating the present invention:

EXAMPLE 1

4-[2-hydroxy-3-(1-methyl-3-nitratopropylamino)-propoxy]-indolinone benzoate 4.1 g. 4-(2,3-Epoxypropoxy)-indolinone (see Federal Republic of Germany Patent Specification No. 33 10 891.9) are suspended in 100 ml. methanol and mixed with 14.6 g. 1-methyl-3-nitratopropylamine. The reaction mixture is stirred for 3 days at ambient temperature, evaporated in a vacuum and the residue taken up in ethyl acetate and extracted several times with water. After drying with anhydrous sodium sulphate, the solution is filtered with suction and the filtrate mixed with the calculated amount of benzoic acid, evaporated in a vacuum and purified over a column of silica gel using methylene chloride/methanol (95/5 v/v). The eluate is evaporated in a vacuum, taken up with a little ethyl acetate and filtered with suction. There are obtained 3.9 g. of the title compound (42% of theory); m.p. 133°–134° C.

The following compounds are obtained in a manner analogous to that described in Example 1:

| designation | yield (%) | m.p. (°C.) solvent |
|---|---|---|
| (a) 4-[2-hydroxy-3-(1,1-dimethyl-3-nitratopropylamino)-propoxy]-indolinone hemifumarate from 4-(2,3-epoxypropoxy)-indolinone and 1,1-dimethyl-3-nitratopropylamine | 10 | 134–136 isopropanol/water |
| (b) 4-[2-hydroxy-3-(1,3-dimethyl-3-nitratopropylamino)-propoxy]-indolinone fumarate from 4-(2,3-epoxypropoxy)-indolinone and 1,3-dimethyl-3-nitratopropylamine | 15 | 149–150 isopropanol |
| (c) 5-[2-hydroxy-3-(1-methyl-3-nitratopropylamino)-propoxy]-indolinone fumarate from 5-(2,3-epoxypropoxy)-indolinone and 1-methyl-3-nitratopropylamine | 15 | 100 (decomp.) ethanol |
| (d) 6-[2-hydroxy-3-(1-methyl-3-nitratopropylamino)-propoxy]-indolinone fumarate from 6-(2,3-epoxypropoxy)-indolinone and 1-methyl-3-nitratopropylamine | 20 | 127–128 ethanol |
| (e) 7-[2-hydroxy-3-(1-methyl-3-nitratopropylamino)-propoxy]-indolinone fumarate from 7-(2,3-epoxypropoxy)-indolinone and 1-methyl-3-nitratopropylamine | 18 | 141–142 ethanol |
| (f) 5-[2-hydroxy-3-(1-methyl-3-nitratopropylamino)-propoxy]-3-isopropylindolinone from 5-(2,3-epoxypropoxy)-3-isopropylindolinone and 1-methyl-3-nitratopropylamine | 25 | 95–97 ethanol |
| (g) 5-[2-hydroxy-3-(1-methyl-3-nitratopropylamino)-propoxy]-3-(α-methylbenzyl)-indolinone hemifumarate from 5-(2,3-epoxypropoxy)-3-(α-methylbenzyl)-indolinone and 1-methyl-3-nitratopropylamine | 25 | 133–135 ethyl acetate |
| (h) 5-[2-hydroxy-3-(1-methyl-3-nitratopropylamino)-propoxy]-3-isopropylideneindolinone from 5-(2,3-epoxypropoxy)-3-isopropylideneindolinone and 1-methyl-3-nitratopropylamine | | |
| (i) 5-[2-hydroxy-3-(1-methyl-3-nitratopropylamino)-propoxy]-3-(α-methylbenzylidene)-indolinone hemifumarate from 5-(2,3-epoxypropoxy)-3-(α-methylbenzylidene)-indolinone and 1-methyl-3-nitratopropylamine | 20 | 155–157 ethanol |

The intermediates required for the preparation of the compounds of Examples (1c), (1d) and (1e) are prepared according to the methods described in European Patent Specification No. 0014928 and in Federal Republic of Germany Patent Specification No. 33 10 891.9.

| designation | yield (%) | m.p. (°C.) solvent |
|---|---|---|
| 5-(2,3-epoxypropoxy)-indolinone | 50 | 129–130 diethyl ether |
| 6-(2,3-epoxypropoxy)-indolinone | 40 | 130–131 ethyl acetate |
| 7-(2,3-epoxypropoxy)-indolinone | 45 | 183 ethyl acetate |

Intermediates used for the preparation of the compounds of Examples (1f), (1g), (1h) and (1i) are prepared in the following manner:

5-Hydroxy-3-isopropylideneindoline

A mixture of 20 g. 5-hydroxyindolinone, 80 ml. acetone and 80 ml. ethanol is saturated with gaseous ammonia and heated under reflux for 3 hours. After evaporation, the reaction mixture is filtered off with suction. There are obtained 27.7 g. of the title compound (94% of theory); m.p. 235° C.

5-Hydroxy-3-(α-methylbenzylidene)-indolinine is obtained analogously; yield 60% of theory; m.p. 175°–178° C., after recrystallisation from diethyl ether.

5-Hydroxy-3-isopropylindolinone 23 g. 5-Hydroxy-3-isopropylideneindolinone are dissolved in 100 ml. ethanol and 150 ml. tetrahydrofuran and hydrogenated in the presence of 1 g. 10% palladium-charcoal at ambient temperature and 1 bar hydrogen pressure. After filtering off the catalyst with suction, the filtrate is distilled off in a vacuum and the residue is triturated with diethyl ether and filtered off with suction. There are obtained 19 g. of the title compound; yield 81% of theory; m.p. 175° C.

5-Hydroxy-3-(α-methylbenzyl)-indolinone is obtained analogously; yield 73% of theory; m.p. 215°–216° C., after recrystallisation from diethyl ether.

5-(2,3-Epoxypropoxy)-3-isopropylindolinone 18 g. 5-Hydroxy-3-isopropylindolinone are dissolved in 150 ml. ethanol, 22 ml. epichlorohydrin are added thereto, the mixture is mixed with 5.3 g. potassium hydroxide in 5 ml. water and the reaction mixture is stirred for 2 days at ambient temperature. After the addition of 200 ml. water, the reaction mixture is extracted with ethyl acetate and the extract purified over a column of silica gel with methylene chloride/methanol (95:5 v/v). There are obtained 11 g. of the title compound; yield 50% of theory; m.p. 122°–125° C., after recrystallisation from diethyl ether.

The following compounds are obtained in analogous manner:

5-(2,3-epoxypropoxy)-3-isopropylideneindolinone; m.p. 167° C.; yield 45% of theory 5-(2,3-epoxypropoxy)-3-(α-methylbenzyl)-indolinone; viscous oil; yield 50% of theory 5-(2,3-epoxypropoxy)-3-(α-methylbenzylidene)-indolinone; m.p. 153°–155° C., after recrystallisation from diethyl ether; yield 64% of theory.

EXAMPLE 2

4-[2-Hydroxy-3-(1-methyl-3-nitratopropylamino)-propoxy]-3-(pyrazol-5-yl)-methyleneindolinone benzoate 3.7 g. 4-(2,3-Epoxypropoxy)-3-(pyrazol-5-yl)-methyleneindolinone (see Federal Republic of Germany Patent Specification No. P 33 10 891.9) are stirred for 3 days at ambient temperature with 100 ml. methanol and 10 g. 1-methyl-3-nitratopropylamine. After removal of the solvent, the residue is dissolved in ethyl acetate and shaken out several times with water. After drying the organic phase over anhydrous sodium sulphate, it is filtered with suction and the filtrate is mixed with the calculated amount of benzoic acid. After suction filtration, there are obtained 2.5 g. of the title compound; yield 35% of theory; m.p. 148°–150° C.

The following compounds are obtained in a manner analogous to that described in Example 2:

| designation | yield (%) | m.p. (°C.) solvent |
|---|---|---|
| (a) 4-[2-hydroxy-3-(1-methyl-3-nitratopropylamino)-propoxy]-3-(pyrrol-2-yl)-methylene-indolinone hemifumarate from 4-(2,3-epoxypropoxy)-3-(pyrrol-2-yl)-methylene-indolinone and 1-methyl-3-nitratopropylamine | 10 | 161–163 ethanol |
| (b) 4-[2-hydroxy-3-(1-methyl-3-nitratopropylamino)-propoxy]-3-(pyridin-2-yl)-methylene-indolinone fumarate from 4-(2,3-epoxypropoxy)-3-(pyridin-2-yl)-methylene-indolinone and 1-methyl-3-nitratopropylamine | 15 | 153–155 ethanol |
| (c) 4-[2-hydroxy-3-(1-methyl-3-nitratopropylamino)-propoxy]-3-benzylideneindolinone fumarate from 4-(2,3-epoxypropoxy)-3-benzylideneindolinone and 1-methyl-3-nitratopropylamine | 20 | 155–158 ethanol |

EXAMPLE 3

4-[24-Hydroxy-3-(1-methyl-3-nitratopropylamino)-propoxy]-indolinone fumarate 38.2 g. Ethyl 2-(2,3-epoxypropoxy)-6-nitrophenyl acetate (see European Patent Specification No. 00 14 928) are dissolved in a mixture of 140 ml. ethyl acetate, 140 ml. ethanol and 30 ml. water, mixed with 3 ml. Raney nickel and hydrogenated at 1 bar hydrogen pressure. After filtering off the catalyst with suction, the filtrate is evaporated, the residue is dissolved in 200 ml. ethanol, 20 g. 1-methyl-3-nitratopropylmine are added thereto and the reaction mixture is stirred for 1 day at ambient temperature. After the addition of 30 ml. acetic acid, the reaction mixture is further stirred for 1 day. The solution is then evaporated and the residue is dissolved in 750 ml. water and 750 ml. ethyl acetate/-diethyl ether (1:1 v/v). The aqueous phase is neutralised with sodium bicarbonate and the base is extracted with ethyl acetate. After drying and evaporating the extract, there is obtained 11 g. of base. This is taken up in isopropanol and the calculated amount of fumaric acid is added thereto to give the salt. After suction filtration, there are obtained 10 g. of the title compound; yield 20% of theory; m.p. 123°–125° C.

By catalytic hydrogenation and subsequent reaction with amines and cyclisation, the following compounds can be obtained in an analogous manner:

| designation | yield (%) | m.p. (°C.) solvent |
|---|---|---|
| (a) 4-[2-hydroxy-3-(1,1-dimethyl-3-nitratopropylamino)-propoxy]-indolinone hemifumarate from 2-(2,3-epoxypropoxy)-6-nitro-phenyl acetic acid ethyl ester and 1,1-dimethyl-3-nitratopropylamine | 15 | 134–136 isopropanol |
| (b) 4-[2-hydroxy-3-(1,3-dimethyl-3-nitratopropylamino)-propoxy]-indolinone fumarate from 2-(2,3-epoxypropoxy)-6-nitro-phenyl acetic acid ethyl ester | 25 | 150 isopropanol |

| designation | yield (%) | m.p. (°C.) solvent |
|---|---|---|
| and 1,3-dimethyl-3-nitratopropylamine | | |
| (c) 5-[2-hydroxy-3-(1-methyl-3-nitratopropylamino)-propoxy]-indolinone fumarate from 3-(2,3-epoxypropoxy)-6-nitro-phenyl acetic acid ethyl ester and 1-methyl-3-nitratopropylamine | 20 | 100–103 ethanol |
| (d) 6-[2-hydroxy-3-(1-methyl-3-nitratopropylamino)-propoxy]-indolinone fumarate from 4-(2,3-epoxypropoxy)-6-nitro-phenyl acetic acid ethyl ester and 1-methyl-3-nitratopropylamine | 20 | 128–129 ethanol |
| (e) 7-[2-hydroxy-3-(1-methyl-3-nitratopropylamino)-propoxy]-indolinone fumarate from 5-(2,3-epoxypropoxy)-6-nitro-phenyl acetic acid ethyl ester and 1-methyl-3-nitratopropylamine | 25 | 141–142 ethanol |

EXAMPLE 4

4-[2-Hydroxy-3-(1-methyl-3-nitraopropylamino)-propoxy]-3-(pyrrol-2-yl)-methyleneindolinone hemifumarate 5.5 g. 4-[2-Hydroxy-3-(1-methyl-3-nitratopropylamino)-propoxy]-indolinone (see Example 1) are stirred in 100 ml. ethanol with 3.4 g. pyrrol-2-aldehyde and 5 ml. triethylamine for 2 days at ambient temperature. After removing the solvent in a vacuum, the residue is dissolved in ethyl acetate and dilute lactic acid. The aqueous phase is rendered alkaline with potassium carbonate and extracted with ethyl acetate. After purification over a column of silica gel with methylene chloride-methanol (97:3 v/v), the hemifumarate is prepared in ethanol. After suction filtration, there is obtained 1.6 g. of the title compound (20% of theory); m.p. 161°–163° C.

The following compounds are prepared in an analogous manner:

| designation | yield (%) | m.p. (°C.) solvent |
|---|---|---|
| (a) 4-[2-hydroxy-3-(1-methyl-3-nitratopropylamino)-propoxy]-3-(furan-2-yl)-methylene-indolinone fumarate from 4-[2-hydroxy-3-(1-methyl-3-nitratopropylamino)-propoxy]-indolinone (see Example 1) and furan-2-aldehyde | 35 | 155–158 ethanol |
| (b) 4-[2-hydroxy-3-(1-methyl-3-nitratopropylamino)-propoxy]-3-(thiophen-2-yl)-methylene-indolinone fumarate from 4-[2-hydroxy-3-(1-methyl-3-nitratopropylamino)-propoxy]-indolinone (see Example 1) and thiophene-2-aldehyde | 30 | 152–153 methanol |
| (c) 4-[2-hydroxy-3-(1-methyl-3-nitratopropylamino)-propoxy]-3-(pyrazol-5-yl)-methylene-indolinone fumarate from 4-[2-hydroxy-3-(1-methyl-3-nitratopropylamino)-propoxy]-indolinone (see Example 1) and pyrazole-5-aldehyde | 25 | 168–170 methanol |
| (d) 4-[2-hydroxy-3-(1-methyl-3-nitratopropylamino)-propoxy]-3-(1,2,4-triazol-3-yl)-methyleneindolinone fumarate from 4-[2-hydroxy-3-(1-methyl-3-nitratopropylamino)-propoxy]-indolinone (see Example 1) and 1,2,4-triazol-3-aldehyde | 40 | 174 methanol |
| (e) 4-[2-hydroxy-3-(1-methyl-3-nitratopropylamino)-propoxy]-3-(pyridin-2-yl)-methylene-indoline fumarate from 4-[2-hydroxy-3-(1-methyl-3-nitratopropylamino)-propoxy]-indolinone (see Example 1) and pyridine-2-aldehyde | 15 | 153–155 ethanol |
| (f) 4-[2-hydroxy-3-(1-methyl-3-nitratopropylamino)-propoxy]-3-(uracil-4-yl)-methylene-indolinone acetate from 4-[2-hydroxy-3-(1-methyl-3-nitratopropylamino)-propoxy]-indolinone (see Example 1) and uracil-4-aldehyde | 15 | 190 methanol |
| (g) 4-[2-hydroxy-3-(1,1-dimethyl-3-nitratopropylamino)-propoxy]-3-(pyrazol-5-yl)-methylene-indolinone hemifumarate from 4-[2-hydroxy-3-(1,1-dimethyl-3-nitratopropylamino)-propoxy]-indolinone (see Example 1a) and pyrazole-5-aldehyde | 25 | 143–145 methanol |
| (h) 4-[2-hydroxy-3-(1,3-dimethyl-3-nitratopropylamino)-propoxy]-3-pyrazol-5-yl)-methylene-indolinone fumarate from 4-[2-hydroxy-3-(1,3-dimethyl-3-nitratopropylamino)-propoxy]-indolinone (see Example 1b) and pyrazole-5-aldehyde | 30 | 70 (decomp.) isopropanol |
| (i) 4-[2-hydroxy-3-(1-methyl-3-nitratopropylamino)-propoxy]-3-benzylideneindolinone fumarate from 4-[2-hydroxy-3-(1-methyl-3-nitratopropylamino)-propoxy]-indolinone (see Example 1) and benzaldehyde | 25 | 155–158 ethanol |
| (j) 4-[2-hydroxy-3-(1-methyl-3-nitratopropylamino)-propoxy]-3-(4-cyanobenzylidene)-indolinone hemifumarate from 4-[2-hydroxy-3-(1-methyl-3-nitratopropylamino)-propoxy]-indolinone (see Example 1) and 4-cyanobenzaldehyde | 20 | 155–157 methanol |
| (k) 4-[2-hydroxy-3-(2,2-dimethyl-3-nitratopropylamino)-propoxy]-3-(3-methylpyrazol-5-yl)-methyleneindolinone from 4-[2-hydroxy-3-(2,2-dimethyl-3-nitratopropylamino)-propoxy]-indolinone and 3-methylpyrazol-5-aldehyde | 80 | 150–151 methanol |

EXAMPLE 5

4-[2-Hydroxy-3-(1-methyl-3-nitratopropylamino)-propoxy]-indolinone fumarate 2.94 g. 4-[2-Hydroxy-3-(1-methyl-3-hydroxypropylamino)-propoxy]-indolinone in 100 ml. acetonitrile are mixed at 30° C., while stirring, with a mixture of 1.16 ml. acetic anhydride, 0.52 ml. fuming nitric acid and 20 ml. acetonitrile. After stirring for 3 hours at −30° C., the reaction mixture is stirred into 300 g. ice water, the pH is adjusted to 8 with 1N aqueous sodium hydroxide solution and then stirred for 2 hours with ethyl acetate at 5° C. The pH is then adjusted to 10 and after 30 minutes the organic phase is separated off. After drying and adding the calculated amount of fumaric acid, there is obtained 0.9 g. of the title compound; yield 20% of theory;

m.p. 122°-124° C.

The above-mentioned hydroxy compound is obtained from ethyl 2-(2,3-epoxypropoxy)-6-nitrophenyl acetate and 1-methyl-3-hydroxypropylamine; yield 50% of theory; m.p. 112°-115° C., after recrystallisation from ethyl acetate.

It will be understood that the specification and examples are illustrative but not limitative of the present invention and that other embodiments within the spirit and scope of the invention will suggest themselves to those skilled in the art.

What is claimed is:

1. An oxindole compound of the formula:

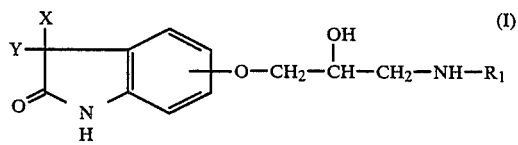

wherein $R_1$ is a $C_2$–$C_{10}$-nitratoalkyl, X is hydrogen or $C_1$–$C_6$-alkyl; Y, together with X and the carbon atom to which they are attached, forms a $C_3$–$C_7$ cycloalkyl ring, or is a group of the formula:

wherein $R_2$ is hydrogen or $R_2$ together with X represents a valency bond, $R_3$ is hydrogen or a straight-chained or branched $C_1$–$C_6$-alkyl and $R_4$ is straight-chained or branched $C_1$–$C_6$-alkyl, $C_3$–$C_6$ cycloalkyl; or phenyl, furan, thiophene, pyrrole, pyrazole, imidazole, triazole, tetrazole, imidazolinone, pyridine, pyrimidine, uracil, indole, indazole and dihydropyran radical which is unsubstituted or substituted by halogen, $C_1$–$C_6$-alkyl, hydroxyalkyl, hydroxyl, $C_1$–$C_6$-alkoxy, $C_2$–$C_4$-alkenyl, $C_2$–$C_4$-alkenyloxy, $C_2$–$C_4$-alkynyl, amino, $C_1$–$C_4$-alkylamino, $C_2$–$C_8$-dialkylamino, aminocarbonyl, $C_1$–$C_4$-alkylaminocarbonyl, $C_2$–$C_8$-dialkylaminocarbonyl, cyano, $C_2$–$C_4$-alkanoyl, aminosulphonyl, $C_1$–$C_4$-alkylaminosulphonyl, $C_2$–$C_8$-dialkylaminosulphonyl, carboxyl, $C_1$–$C_6$-alkoxycarbonyl, $C_1$–$C_6$-alkylthio, $C_1$–$C_6$-alkylsulphinyl, $C_1$–$C_6$-alkylsulphonyl, $C_2$–$C_4$-alkanoylamido, $C_1$–$C_4$-alkylsulphonylamido or nitro groups or a $C_1$–$C_2$-alkylenedioxy radical or $R_3$ and $R_4$ together with the C-atom represent pyrrolidine or piperidine; or a pharmacologically acceptable salt thereof.

2. The compound of claim 1 wherein $R_1$ is selected from the group consisting of nitratoethyl, nitratopropyl, nitratobutyl, nitratopentyl, nitroatohexyl, 1-methyl-2-nitratoethyl 1-methyl-3-nitratopropyl, 1,1-dimethyl-3,-nitratopropyl, 1,3-dimethyl-3-nitratopropyl or 2,2-dimethyl-3-nitratopropyl.

3. The compound of claim 1 wherein the $C_1$–$C_6$-alkyl in the substituents $R_3$, $R_4$, $R_5$, X are individually selected from the group consisting of methyl, ethyl, isopropyl, and tert.-butyl.

4. The compound of claim 1 wherein $R_4$ is phenyl or phenyl substituted by halogen, $C_1$–$C_6$-alkyl, hydroxyalkyl, hydroxyl, $C_1$–$C_6$-alkoxy, $C_2$–$C_4$-alkenyl, $C_2$–$C_4$-alkenyloxy, $C_2$–$C_4$-alkynyl, amino, $C_1$–$C_4$-alkylamino, $C_2$–$C_8$-dialkylamino, aminocarbonyl, $C_1$–$C_4$-alkylaminocarbonyl, $C_2$–$C_8$-dialkylaminocarbonyl, cyano, $C_2$–$C_4$-alkanoyl, aminosulphonyl, $C_1$–$C_4$-alkylaminosulphonyl, $C_2$–$C_8$-dialkylaminosulphonyl, carboxyl, $C_1$–$C_6$-alkoxycarbonyl, $C_1$–$C_6$-alkylthio, $C_1$–$C_6$-alkylsulphinyl, $C_1$–$C_6$-alkylsulphonyl, $C_2$–$C_4$-alkanoylamido, $C_1$–$C_4$-alkylsulphonylamido, $C_1$–$C_2$-alkylenedioxy or nitro groups.

5. The compound of claim 1 wherein $R_3$ is hydrogen or methyl and $R_4$ is phenyl, pyrazole, pyrrole, furan, thiophene, triazole, pyridine or uracil, which is unsubstituted or substituted by $C_1$–$C_6$-alkyl, cyano, nitro, halogen or $C_1$–$C_6$ alkoxy or $R_3$ and $R_4$ together with the carbon atom represent pyrrolidine or piperidine.

6. The compound of claim 1 designated 4-[2-hydroxy-3-(1-methyl-3-nitratopropylamino)-propoxy]-3-benzylideneindolinone.

7. The compound of claim 1 designated 4-[2-hydroxy-3-(1-methyl-3-nitratopropylamino)-propoxy]-3-(pyrazol-5-yl)-methyleneindolinone.

8. The compound of claim 1 designated 4-[2-hydroxy-3-(1-methyl-3-nitratopropylamino)propoxy]-3-(3-methyl-pyrazole-5-yl)methylene-indolinone.

9. The compound of claim 1 designated 4-[2-hydroxy-3-(1,1-dimethyl-3-nitratopropylamino)-propoxy]-3-(pyrazol-5-yl)-methyleneindolinone.

10. The compound of claim 1 designated 4-[2-hydroxy-3-(1-methyl-3-nitratopropylamino)-propoxy]-3-(pyridin-2-yl)-methyleneindolinone.

11. The compound of claim 1 designated 4-[2-hydroxy-3-(1-methyl-3-nitratopropylamino)propoxy]-3-(4-nitro-benzylidene)indolinone.

12. The compound of claim 1 wherein $C_3$–$C_7$ cycloalkyl rings formed by X and Y and the carbon to which they are attached are selected from the group consisting of cyclopropyl, cyclopentyl, cyclohexyl and cycloheptyl.

13. A pharmaceutical composition for the treatment of heart and circulatory diseases that respond to a lowering of blood pressure, a positive inotropic action, an improvement in microcirculation or a combination thereof, comprising an effective amount, for the treatment and prophylaxis of such heart and circulatory diseases, of the compound of claim 1 in a pharmaceutically acceptable carrier.

* * * * *

UNITED STATES PATENT AND TRADEMARK OFFICE
CERTIFICATE OF CORRECTION

PATENT NO. : 4,826,847

DATED : May 2, 1989

INVENTOR(S) : Helmut Michel, et al.

It is certified that error appears in the above-identified patent and that said Letters Patent is hereby corrected as shown below:

Col. 7, line 14:   delete "indolinon" and insert -- indolinone --.

Col. 7, line 55:   delete "137+ C" and insert -- 137 C --.

Col. 8, line 12:   delete "3-nitropropylamino" and insert -- 3-nitratopropylamino --.

Col. 12, line 29:  delete "4-[24-Hydroxy" and insert -- 4-[2-Hydroxy --.

Col. 12, line 31:  delete "38.2 g Ethyl" and insert -- 28.2 g Ethyl --.

Col. 12, line 38:  delete "nitratopropylmine" and insert -- nitratopropylamine --.

Signed and Sealed this

Twenty-sixth Day of June, 1990

*Attest:*

HARRY F. MANBECK, JR.

*Attesting Officer*   *Commissioner of Patents and Trademarks*